(12) United States Patent
Mailland

(10) Patent No.: US 8,906,881 B2
(45) Date of Patent: *Dec. 9, 2014

(54) USE OF CHITOSANS FOR THE TREATMENT OF NAIL INFLAMMATORY DISEASES

(75) Inventor: Federico Mailland, Milan (IT)

(73) Assignee: Polichem SA, Luxembourg (LU)

( * ) Notice: Subject to any disclaimer, the term of this patent is extended or adjusted under 35 U.S.C. 154(b) by 126 days.

This patent is subject to a terminal disclaimer.

(21) Appl. No.: 12/449,540

(22) PCT Filed: Feb. 7, 2008

(86) PCT No.: PCT/EP2008/051479
§ 371 (c)(1),
(2), (4) Date: Aug. 12, 2009

(87) PCT Pub. No.: WO2008/098871
PCT Pub. Date: Aug. 21, 2008

(65) Prior Publication Data
US 2010/0104670 A1    Apr. 29, 2010

(30) Foreign Application Priority Data

Feb. 14, 2007  (EP) .................................. 07102338

(51) Int. Cl.
*A61K 31/726* (2006.01)
*A61K 36/00* (2006.01)
(52) U.S. Cl.
USPC ............... 514/55; 514/54; 514/782; 514/777; 106/162.2; 424/725; 424/195.18
(58) Field of Classification Search
USPC ......... 424/725, 195.18; 514/54, 782, 777, 55; 106/162.2
See application file for complete search history.

(56) References Cited

U.S. PATENT DOCUMENTS

| 3,929,768 | A | 12/1975 | Brattsand |
| 4,780,310 | A | 10/1988 | Lang et al. |
| 6,740,326 | B1* | 5/2004 | Meyer et al. ................... 424/401 |
| 7,033,578 | B2 | 4/2006 | Mailland |
| 2001/0001788 | A1 | 5/2001 | Satoh et al. |
| 2003/0147890 | A1* | 8/2003 | Ye ................. 424/145.1 |
| 2004/0137041 | A1* | 7/2004 | You et al. ....................... 424/443 |

(Continued)

FOREIGN PATENT DOCUMENTS

| DE | 2323215 | 11/1973 |
| EP | 1491202 | 12/2004 |

(Continued)

OTHER PUBLICATIONS

Muzzarelli et al. Chitosan Chemistry: Relevance to the Biomedical Sciences; Adv. Polym Sci (2005) 186, pp. 151-209.*

(Continued)

*Primary Examiner* — Patricia Leith
(74) *Attorney, Agent, or Firm* — Hueschen and Sage

(57) ABSTRACT

Chitosan-based nail formulations are useful to treat nail inflammatory diseases like psoriasis, atopic dermatitis and *lichen planus*. The chitosan is normally in the form of an amino-polysaccharide derivative, preferably water soluble, such as hydroxypropyl chitosan. The formulation may be a nail lacquer, a spray, a cream, an ointment, a gel, a lotion or a foam and may have a content in chitosan, chitosan derivative or a salt thereof from 0.1 to 25 wt. % with respect to the total weight of the formulation.

13 Claims, 1 Drawing Sheet

Time course of the quality of life (DLQI score) in 28 patient with nail psoriasis, during treatment with composition as per the Example 7.

(56) References Cited

U.S. PATENT DOCUMENTS

| | | | |
|---|---|---|---|
| 2006/0110342 A1* | 5/2006 | Dechow | 424/61 |
| 2006/0134039 A1* | 6/2006 | Mailland | 424/70.1 |
| 2006/0194760 A1 | 8/2006 | Griesbach et al. | |

FOREIGN PATENT DOCUMENTS

| | | |
|---|---|---|
| EP | 1842545 | 10/2007 |
| JP | 2002539144 | 11/2002 |
| JP | 2004504333 | 1/2004 |
| JP | 2006232773 | 9/2006 |
| WO | 98/26788 | 6/1998 |
| WO | 03/051376 | 6/2003 |
| WO | 2006/111426 | 10/2006 |
| WO | WO2006134614 | 12/2006 |
| WO | 2007/042682 | 4/2007 |
| WO | 2008/049401 | 5/2008 |

OTHER PUBLICATIONS

Database WPI, Sep. 24, 1996, Thompson Scientific, XP002441653, "JP 08 245401, Sep. 24, 1996".

Database WPI, Aug. 20, 2005, Thompson Scientific, XP002441654, "RU 2 258 516, Aug. 20, 2005".

Database WPI May 15, 2001, Thompson Scientific, XP002441655, "JP 2001 131030, May 15, 2001".

International Search Report for PCT/EP2008/051479 of Aug. 12, 2008.

Haneke, E. JDDG, 7:787-797, 2009.

Chen, et al. Wound Repair and Regeneration, Mar.-Apr., pp. 79-89, 1999.

Sparavigna, et al. Journal of Plastic Dermatology 4:1-8, 2008.

Tosti, A., et al., Catcipotriol ointment in nail psoriasis: a controlled double-blind comparison with betamethasone dipropionate and salicyclic acid. British Journal of Dermatology, 1998, vol. 139, pp. 655-669.

Zakeri, M., et al., Topical calcipotriol therapy in nail psoriasis: A study of 24 cases. Dermatology Online Journal, vol. 11, No. 3, pp. 1-3, 2005.

Baran and Dawber's, Diseases of the Nails, Edited by R. Baran, et al. Third Edition, Blackwell Science Ltd. p. 78, 2001.

Baran and Dawber's, Diseases of the Nails, Edited by R. Baran, et al. Third Edition, Blackwell Science Ltd. pp. 172-177, 2001.

Kyriakou, et al. Journal of Dermatological Treatment. pp. 1-9, 2012.

Vergou, et al. Expert Rev. Clin. Pharmacol. 4:515-523, 2011.

* cited by examiner

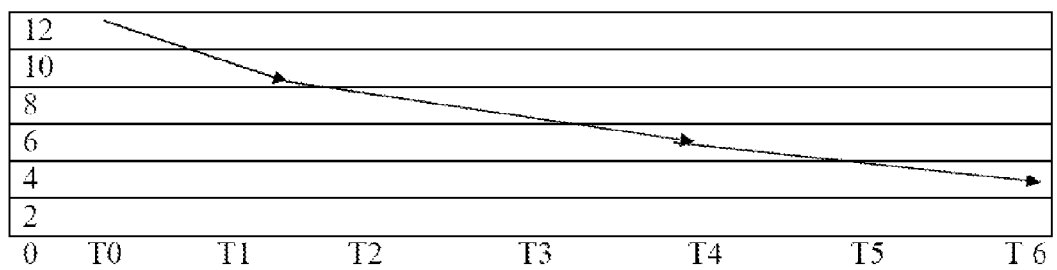
Time course of the quality of life (DLQI score) in 28 patient with nail psoriasis, during treatment with composition as per the Example 7.

USE OF CHITOSANS FOR THE TREATMENT OF NAIL INFLAMMATORY DISEASES

The present invention relates to use of chitosan, a chitosan derivative or a physiologically acceptable salt thereof, for the preparation of a medicament, or a medical device, or a sanitary product, or a cosmetic, in form of a nail lacquer, useful for the topical treatment of inflammatory diseases of the nails, such as psoriasis, *lichen planus* and atopic dermatitis.

Psoriasis is a genetically predetermined hyperproliferative skin disease, characterized by increased cell proliferation, glycogen accumulation and incomplete differentiation in the cells of the epidermis. Nail involvement in psoriasis is common and has been reported in between 50% and 56% of cases. It is estimated that over a lifetime between 80% and 90% of psoriatic patients will suffer nail localization of psoriasis (de Berker, Baran & Dawber: the nail in dermatological disease. In: Baran & Dawber's: *Diseases of the nails and their management*. Baran et al Eds, $3^{rd}$ ed. Blackwell Science, 2001). Overall, 58% of patients with nail psoriasis consider that this condition interferes with their job and 52% describe pain as a symptom. Nail psoriasis is affecting adults and children. In children, nail involvement has been found to range between 7% and 39% according to the different authors. In children with juvenile psoriatic arthritis, 80% of children developed pitting, a nail manifestation of psoriasis.

Severe nail involvement may not imply severe psoriasis of the skin and the type of the nail change is not associated with any particular distribution of the skin lesions. The clinical signs of psoriasis can be correlated with the site of involvement of the epidermal structures of the nail. The main psoriatic features in the nails are, in order of frequency:

1) pitting: pits are punctate depressions, usually small and shallow, that can vary in size, depth and shape. They originate from focal psoriasis of the proximal matrix (the region where the nail is formed). Most pits are superficial, and when extensive they can produce gross abnormalities in colour and texture, and can render the nail fragile. Histologically, pits represent a defect in superficial layers of the nail plate and when the psoriasis becomes more marked, a pit may enlarge and produce a hole in the nail plate.
2) discoloration of the nail: typical pictures are leuconychia (white nail appearance), when the nail matrix is involved, or salmon colour when the nail bed is involved. Psoriasis in the nail bed produces oval, salmon coloured, oily spots of various size.
3) onycholysis: this is a detachment of the nail plate from the nail bed. This occurs mainly when oily spots affect the hyponychium (the part under the nail plate) medially or laterally. Onycholytic nail has a yellowish colour, due to a combination of air and the accumulation of squames under the nail interface.
4) subungual hyperkeratosis: this is a thickening of the tissues under the nail plate. It is manifested as accumulated squames, and is an expression of the alteration of the keratin composition in nail bed psoriasis.
5) nail plate abnormalities: they include serial transverse depression, especially on the thumbs where they mimic washboard nails. Other common abnormalities are longitudinal ridges of the nail with bumps that resemble drops of melted wax.
6) splinter haemorrhages: they occur in fingernails of 42% of psoriatic patients with nail disease and in 6% of their toenails. The sign reflects the orientation of the capillary vessels in the nail bed and the proliferation and fragility of these capillaries in active psoriasis.

There may be psoriatic scaling of the proximal nail fold with soft tissue swelling or chronic paronychia. The changes observed in the nail plate depend on the location and duration of the disease process. The lesions may reflect transient matrix dysfunction and be limited in extent, such as pits and transverse furrows. Alternatively, they may represent persistent disease and result in sustained nail abnormalities, such as loss or thickening of the nail plate. Besides the aesthetic appearance, the psoriatic nails are fragile and painful, and patients are prevented from their daily life activities.

The treatment of the nail psoriasis includes systemic and/or topical therapies. Systemic therapies include potent corticosteroids, Vitamin D analogues, retinoids or immunosuppressive agents, and are generally avoided due to their potential toxicity, unless the patient presents a very severe, generalized psoriasis.

Topical therapies are mainly for application to the base of the nail. At this site, they may treat psoriasis of the nail fold and penetrate through the underlying matrix to a limited extent. Some of the transverse ridging in the psoriatic nails is associated with inflammation of the proximal nail fold. If this is reduced, the matrix function returns towards normal and nail ridging diminishes. If onycholysis is present, the nail plate must be trimmed back to the point of separation.

Topical products used in psoriasis are the following:
1. corticosteroids: fluocinolone acetonide, triamcinolone acetonide, bethametasone salts, clobetasol propionate, are known in the art. All of them are applied under occlusive medication, and side effects such as distal phalangeal dystrophy have been reported (Deffer & Goette *Archives of dermatology*, 1987, 123:571-572. Requena et al. *Archives of dermatology*, 1990, 126:1013-1014).
2. calcipotriol: according to some literature reports (Kokely et al., 1994, *J. Dermatol. Tretment*, 5:149-150) topical calcipotriol may be useful as treatment of nail psoriasis. The limit of this therapy is represented by need of occlusive medication, which is bothersome for the patients, and risk of severe systemic side effects, due to the impairment of renal function and calcium metabolism, thus this drug is not recommended e.g. in children.
3. cyclosporin: topical cyclosporin was used in a single subject, applying a 10% oily preparation under occlusive medication for several months, with clinical benefit (Tosti A., *Dermatologica*, 1990, 180:110).
4. retinoids: topical use under occlusive medication of a tazarotene cream gave clinical benefit (Bianchi et al. *Br J Dermatol*. 2003, 149:207-9).

All topical treatments of nail psoriasis in the art are characterized by the need of occlusive medication, which is bothersome for the patient, impairs their quality of life and may be applied in practice only in the night hours. Thus, there is a strong unsatisfied need for new effective therapeutic agents, simple to use and safe enough to allow chronic use by patients. *Lichen planus* is also an inflammatory disease of the skin, with evidence of a genetic susceptibility, probably due to an immune imbalance, often associated with systemic involvement (de Berker, Baran & Dawber: the nail in dermatological disease. In: Baran & Dawber's: *Diseases of the nails and their management*. Baran et al Eds, $3^{rd}$ ed. Blackwell Science, 2001).

*Lichen planus* may involve the nail plate by appearing in the following clinical subtypes:
1) typical *lichen planus*
2) twenty nail dystrophy
3) idiopathic atrophy of the nails When a nail fold disease is present, this indicates that the proximal nail matrix is involved and nail plate changes are likely to occur soon afterwards. The nail gradually reflects the disease process with a longitudinal red line indicating a thinning nail plate, evolving to distal splitting, where it is most fragile. The next stage is complete split.

Ulceration, hemorrhagic erosions and scarring may appear. Pitting is also a manifestation of *lichen planus* of the proximal nail matrix. *Lichen planus* seldom involves exclusively the nail bed and features of nail bed disease include hyperkeratosis and onycholysis.

The prognosis depends on the degree of matrix involvement and scarring. Complete involvement of nail matrix and nail bed will produce a total loss of the nail plate and permanent atrophy with scarring. Treatment is symptomatic, including oral corticosteroids, retinoids and azathioprine. Severe non-scarring types may be helped by topical treatment with potent corticosteroids.

Of course, nail inflammatory diseases are chronic conditions, that do not respond definitely to a therapeutic treatment. Thus, as for skin, the ideal treatment is lifelong and is put in practice as two or more therapeutic cycles per year for the patient's life.

Chitosan derivatives are amino-polysaccharides, derived from the chitin extracted from the exoskeleton of the crustaceans, known in the art for their use in different preparations for skin. KR20020084672 discloses chitosan as an ingredient of microspheres, useful as a carrier for separation of proteins or peptides; KR20020048534 reports chitosan as an ingredient of a pack composition for skin massage, including paraffin wax as an effective component; JP2005306746 is teaching the use of chitosan to obtain a wrinkle therapeutic agent as an ingredient of gel-like or spongy preparations of botulinus toxin. WO2005055924 reports chitosan derivatives as ingredients of hydrogels useful for cavity-filling wound dressings. JP2004231604 teaches compositions of chitosans having a high deacetylation degree, as an ingredient of a carrier sheet with a porous spongy texture. WO03042251 discloses compositions comprising chitosan in the form of a network of nano-sized fibres. WO02057983 discloses a multi-layered, air gap sheet of chitosan with a regular lamellar structure which retains drugs for a prolonged period of time; JP11060605 teaches an amphiphilic chitosan derivative which can be used as dispersion stabilizer or emulsifier in a drug for application to skin. US2004043963 discloses chitosan conjugated linoleic acid and a chitosan conjugated Vitamin A for the preparation of compositions for treatment of inflammatory skin diseases, including atopic dermatitis, eczema and psoriasis. Moreover, EP1303249 reports the use of water soluble chitosan derivatives as film forming ingredients of nail lacquers, including antimycotic agents for the treatment of nail fungal infections, whereas WO2004/112814 discloses a nail restructuring composition based on one herb extract from the genus *Equisetum* in combination with hydroxypropylchitosan, which is used as a film forming agent. The use of chitosans as film forming agents is also disclosed in WO2006111426 and in WO2007042682.

WO03051376 discloses the use of chitosan oligomers having a molecular weight of less than 10000 Da for preventing or reducing inflammation or hypersensitivity.

None of the references known in the art reports any activity of chitosans or chitosan amino-polysaccharides in nail inflammatory diseases, chitosans having being used until now as carriers of actives in various diseases or as a film forming agent in mycotic infections.

It has now surprisingly been found that chitosans, chitosan amino-polysaccharides and/or physiologically acceptable salts thereof, are useful for the topical treatment of inflammatory diseases of the nails, such as psoriasis, *lichen planus*, alopecia areata and atopic dermatitis. Chitosans and chitosan amino-polysaccharides permeate the keratin structures and reach the nail matrix, where the defect of keratinisation occurs during inflammatory diseases, by decreasing inflammation at that level, thus by allowing the growth of a healthy, smooth nail. When chronically applied onto the nail surface, nail lacquers containing chitosan or its derivatives result in a decrease or disappearance of pitting and of desquamation, thus rendering the nail less fragile and reducing pain.

Nail lacquers based on chitosan and/or chitosan derivatives, such as chitosan amino-polysaccharides, are simple to use and safe enough to allow chronic application by patients. Moreover, the nail lacquers may contain other agents active on nail inflammation, thus strengthening their activity and allowing a long lasting adherence to the nail surface, suitable for long lasting release to the nail, avoiding occlusive medications.

DESCRIPTION OF THE INVENTION

The object of the present invention is the use of chitosan, a chitosan amino-polysaccharide and/or a physiologically acceptable salt thereof, for the topical treatment of inflammatory diseases of the nails, such as psoriasis, *lichen planus* and atopic dermatitis.

The preferred chitosan amino-polysaccharides are water soluble and have a molecular weight higher than 50000 Da, preferably of from 100000 to 500000 Da; among them hydroxyalkyl chitosans, such as hydroxypropyl chitosan, and carboxyalkyl chitosans are particularly preferred.

Nail lacquers based on chitosan or chitosan amino-polysaccharides, in the form of solutions, emulsions, colloids, or suspensions, with a content in chitosan or chitosan amino-polysaccharide from 0.1 to 10 wt. %, more preferably from 0.2 to 5 wt. %, most preferably from 0.3 to 2.0%, are suitable to significantly improve the nail dystrophy in patients with inflammatory diseases of the nails, such as nail localization of psoriasis, by decreasing fragility, pain and pitting, and improving the cosmetic appearance of the nails.

Pharmaceutical compositions will be prepared according to conventional techniques, using compatible excipients and pharmaceutically acceptable carriers, and may contain, in combination, other active principles with complementary or, in any case, useful activity. Examples of these compositions prepared according to the present invention include: solutions, emulsions, suspensions, colloids, for application to nails.

The compositions according to the present invention may contain one or more active agents from corticosteroids, immununo-suppressants, antipsoriatic agents, keratolytics, retinoids, plant extracts, and are suitable to treat nail inflammatory diseases, such as psoriasis, atopic dermatitis, and *lichen planus*.

Examples of corticosteroids which may be included in the composition in accordance with the present invention include 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g. acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivatives thereof, e.g. acetonide, benetonide, diacetate, hexacetonide.

Examples of immunosuppressant agents which may be included in the composition in accordance with the present invention include: cyclosporin, tacrolimus, pimecrolimus and sirolimus.

Examples of antipsoriatic agents which may be included in the composition in accordance with the present invention include: anthracene derivatives, such as dithranol; psoralens, like trioxsalen or methoxsalen; Vitamin D3 analogues, like calcitriol, calcipotriol or tacalcitol; retinoids, like retinoic acid, tretinoin, isotretinoin, etretinate and acitretin, tazarotene; fumaric acid and esters thereof, e.g. monomethyl ester, dimethyl ester. Keratolytics are peeling agents, useful to remove the horny outer layer of the skin, i.e. to promote the removal of dead skin cells from the *stratum corneum*. Examples of keratolytics which may be included in the composition in accordance with the present invention include: salicylic acid; benzoyl peroxide.

The compositions according to the present invention are applied onto the nail surface by brush, or by a plate applicator, or by spray.

The pharmaceutical compositions and the uses of the present invention will now be more fully described by the following examples. It should, however, be noted that such examples are given by way of illustration and not of limitation.

EXAMPLE 1

A nail lacquer having the following composition wt./wt. % is prepared:

| | |
|---|---|
| 1. purified water | 21.0% |
| 2. ethanol | 73.0% |
| 3. ethyl acetate | 4.0% |
| 4. hydroxypropyl chitosan (HPCH) | 1.0% |
| 5. cetostearyl alcohol | 1.0% |

Preparation

The formulation is prepared by using a closed vessel with a stirrer. To this vessel are added ethanol, deionized water and ethyl acetate to form a mixture. Thereafter, cetostearyl alcohol is added. Finally, hydroxypropyl chitosan is added and the resulting mixture is stirred for 24 hours or until dissolution.

The obtained composition has a clear and homogenous appearance even after prolonged storage. Moreover, when applied on the nails, the liquid is able to form a matte, non-sticky and elastic film which could strongly adhere to the nail surface.

EXAMPLE 2

A nail lacquer having the following composition wt./wt. % is prepared:

| | |
|---|---|
| 1. purified water | 29.375% |
| 2. ethanol 96° | 70.0% |
| 3. budesonide | 0.025% |
| 4. hydroxypropyl chitosan (HPCH) | 0.5% |
| 5. Peg-40 Hydrogenated castor oil | 0.1% |

Preparation

The formulation is prepared as per the Examples 1 and 3, by adding hydroxypropyl chitosan as the final ingredient and stirring for 24 hours or until dissolution.

EXAMPLE 3

A nail lacquer having the following composition wt./wt. % is prepared:

| | |
|---|---|
| 1. propylene glycol | 13.0% |
| 2. isopropanol | 82.497% |
| 3. calcitriol | 0.003% |
| 4. ethyl acetate | 4.0% |
| 5. chitosan | 0.5% |

Preparation

Chitosan is dissolved in propylene glycol, then calcitriol previously dissolved in isopropanol is added. Then ethyl acetate is added and the resulting mixture is stirred until dissolution.

EXAMPLE 4

A nail lacquer having the following composition wt./wt. % was prepared:

| | |
|---|---|
| 1. purified water | 29.35% |
| 2. ethanol 96° | 70.00% |
| 3. hydroxypropyl chitosan (HPCH) | 0.50% |
| 4. betamethasone-17-valerate | 0.05% |
| 4. PEG-40 hydrogenated castor oil | 1.00% |

Preparation

The formulation was prepared by using a suitable closed vessel provided with a stirrer. To this vessel were added ethanol, betamethasone-17-valerate and PEG-40 hydrogenated castor oil. The mixture was stirred and then water was added. After short stirring hydroxypropyl chitosan was added. The mixture was stirred for 24 hours until complete dispersion of hydroxypropyl chitosan. The resulting composition is limpid, colourless liquid, with typical alcoholic odour.

EXAMPLE 5

A nail lacquer having the following composition wt./wt. % was prepared:

| | |
|---|---|
| 1. purified water | 29.0% |
| 2. ethanol 96 | 60.0% |
| 3. hydroxypropyl chitosan (HPCH) | 0.5% |
| 4. cyclosporine | 5.0% |
| 5. urea | 5.0% |
| 6. Polyethylenlycol 400 | 0.5% |

Preparation

The formulation was prepared by using a suitable closed vessel provided with a stirrer. To this vessel were added water, ethanol, and after short stirring cyclosporine. The complete dissolution was immediate. Then urea was added, and, after dissolution, Polyethylenglycol 400 was added. After 10 min stirring hydroxypropyl chitosan was added. The mixture was stirred for 8 hours until complete dissolution of hydroxypropyl chitosan. The resulting composition was a limpid, colourless liquid, even after prolonged storage.

Moreover, the liquid was able to form a matte, non-sticky and elastic film which could strongly adhere to the nail surface.

EXAMPLE 6

A nail lacquer having the following composition wt./wt. % was prepared:

| | |
|---|---|
| 1. purified water | 19.45% |
| 2. propylene glycol | 10.00% |
| 2. isopropanol | 70.00% |
| 3. chitosan | 0.50% |
| 4. bechlometasone dipropionate | 0.05% |

Preparation

The formulation was prepared by dissolving chitosan and bechlometasone dipropionate in propylene glycol, then adding the other ingredients, and stirring the mixture until dissolution. The resulting liquid was able to form an elastic film which could strongly adhere to the skin surface.

EXAMPLE 7

A nail lacquer having the following composition wt./wt. % was prepared:

| | |
|---|---|
| 1. purified water | 52.0% |
| 2. ethanol | 36.5% |
| 3. diethylenglycole monomethyleter | 0.5% |
| 4. methylsulphonylmethane (DMSO$_2$) | 5.0% |
| 5. hydroxypropyl chitosan (HPCH) | 1.0% |
| 6. Equisetum arvense glycolic extract | 5.0% |

Preparation

The formulation was prepared by using a suitable closed vessel provided with a stirrer. To this vessel were added ethanol, deionized water and diethyleneglycol-monomethylether to form a mixture. Thereafter, after dissolution thereof, *Equisetum arvense* glycolic extract and methylsulphonyl methane were added. Finally, hydroxypropyl chitosan was added and the resulting mixture was stirred for 24 hours or until dissolution.

The obtained nail lacquer composition had a clear and homogeneous appearance and a yellowish color even after prolonged storage. Moreover, the lacquer was able to form a matte, non-sticky and plastic film which could strongly adhere to the nails. When applied, the moisture and air permeable lacquer did not burn or cause irritation on the adjacent skin or the periungual bed.

EXAMPLE 8

An open, controlled clinical study was performed to assess the efficacy and the safety profile of the nail lacquer according to the Example 7 on patients with nail psoriasis. The involved patients were 20 women and 10 men, aged between 18 and 75 years (mean 46.5 yrs) affected by nail psoriasis, with symmetric lesions of both sides. The nail alterations were manifest from 6 months-2 years prior to the inclusion into the study, with the following clinical characteristics: presence of pitting=15%; presence of onycholysis=9%; presence of leuchonychia=6%. The severity of the nail psoriasis, measured by the NAPSI score (Nail psoriasis severity index, according to Baran R., *Br J Dermatol*, 2004, 150:568-569; Parrish et al., *J Am Acad Dermatol*, 2005, 53:745-476), was between 2 and 5. The nail lacquer according to the Example 7 was applied once daily by the patients on the fingernails of the left hand for 24 consecutive weeks. No other systemic or topical antipsoriatic treatment was taken by the patients during the whole treatment period. At the end, the therapeutic efficacy was judged by the investigator by a clinical examination at cold light, and compared to the fingernails of the right hand. At the end of 24 treatment week, the result of the treated fingernails was judged as "excellent" in 18 cases, "good" in 5 cases and "none" in 5 cases, while the untreated hands were unmodified compared to baseline. The remaining 2 cases were lost to follow up. The quality of life of patients, measured by Dermatology Life Quality Index (DLQI) is a simple 10-question validated Quality of Life questionnaire (Finlay & Khan: *Clinical and Experimental Dermatology*, 1994, 19:210-216 related to the treated hand, also resulted as much improved at the end of treatment compared to baseline (FIG. 1).

During the study, no adverse events occurred, and tolerability of the product according to the Example 7 was judged as optimal by 100% of patients. The judgement of the patients was always very satisfactory both for the treatment easiness and for the organoleptic characteristics of the product.

The invention claimed is:

1. A method of treating nail psoriasis comprising administering to the nail of a human or animal subject, a composition consisting essentially of a chitosan amino-polysaccharide and/or a physiologically acceptable salt thereof, in an amount effective for reducing pitting, nail plate abnormalities and subungual hyperkeratosis.

2. The method of claim 1, wherein the chitosan amino-polysaccharide and/or a physiologically acceptable salt thereof is water soluble.

3. The method of claim 2, wherein the chitosan amino-polysaccharide and/or a physiologically acceptable salt thereof exhibits a molecular weight greater than 50,000 Daltons.

4. The method of claim 2, wherein the chitosan amino-polysaccharide and/or a physiologically acceptable salt thereof exhibits a molecular weight from 100,000 to 500,000 Daltons.

5. The method of claim 2, wherein the chitosan amino-polysaccharide and/or a physiologically acceptable salt thereof is a hydroxyalkyl chitosan.

6. The method of claim 5, wherein the hydroxyalkyl chitosan is a hydroxypropyl chitosan.

7. The method of claim 2, wherein the chitosan amino-polysaccharide and/or a physiologically acceptable salt thereof is a carboxyalkyl chitosan.

8. The method of claim 1, wherein the chitosan amino-polysaccharide and/or a physiologically acceptable salt thereof is administered topically.

9. The method of claim 8, wherein the chitosan amino-polysaccharide and/or a physiologically acceptable salt thereof is administered by means of a topical formulation.

10. The method of claim 9, wherein the topical formulation is a nail lacquer, a spray, a cream, an ointment, a gel, a lotion or a foam.

11. The method of claim 9, wherein the topical formulation comprises a chitosan amino-polysaccharide and/or a salt thereof, from 0.1 to 25 wt. % with respect to the total weight of the formulation.

12. The method of claim 9, wherein the topical formulation comprises a chitosan amino-polysaccharide and/or a salt thereof, from 0.3 to 10 wt % with respect to the total weight of the formulation.

13. The method of claim 9, wherein the topical formulation comprises a chitosan amino-polysaccharide and/or a salt thereof, from 0.5 to 5 wt. % with respect to the total weight of the formulation.

* * * * *

UNITED STATES PATENT AND TRADEMARK OFFICE
CERTIFICATE OF CORRECTION

PATENT NO. : 8,906,881 B2  
APPLICATION NO. : 12/449540  
DATED : December 9, 2014  
INVENTOR(S) : Federico Mailland Page 1 of 1

It is certified that error appears in the above-identified patent and that said Letters Patent is hereby corrected as shown below:

On The Title Page, item (56)

Page 2, Other Publications: Please add the following missing reference

"MUZZARELLI, et al., Chitosan Chemistry: Relevance to the Biomedical Sciences, Adv. Polym. Sci. (2005) 186, Pg. 151-209"

Signed and Sealed this  
Twenty-second Day of September, 2015

Michelle K. Lee  
*Director of the United States Patent and Trademark Office*